US007005441B2

(12) United States Patent
Hines et al.

(10) Patent No.: US 7,005,441 B2
(45) Date of Patent: Feb. 28, 2006

(54) COMPOSITIONS THAT BIND ANTITERMINATOR RNA AND ASSAY FOR SCREENING SUCH COMPOSITIONS

(75) Inventors: Jennifer V. Hines, Athens, OH (US); Stephen C. Bergmeier, Athens, OH (US); Tina M. Henkin, Dublin, OH (US); Frank J. Grundy, Dublin, OH (US)

(73) Assignee: Ohio University, Athens, OH (US)

( * ) Notice: Subject to any disclaimer, the term of this patent is extended or adjusted under 35 U.S.C. 154(b) by 0 days.

(21) Appl. No.: 10/226,614

(22) Filed: Aug. 23, 2002

(65) Prior Publication Data

US 2003/0119031 A1   Jun. 26, 2003

Related U.S. Application Data

(60) Provisional application No. 60/314,898, filed on Aug. 24, 2001.

(51) Int. Cl.
*A61K 31/422* (2006.01)
*C07D 263/06* (2006.01)

(52) U.S. Cl. ..................... 514/376; 548/232
(58) Field of Classification Search ............... 514/376; 548/232
See application file for complete search history.

(56) References Cited

OTHER PUBLICATIONS

Grundy, et al., "tRNA-mediated transcription antitermination in vitro : Codon-anticodon pairing independent of ribosome", PNAS, Aug. 20, 2002, vol. 99, No. 17, pp. 11121-11126.
Gerdeman, et al., "Solution Structure of the *Bacillus subtillis* T-box Antiterminator RNA: Seven Nucleotide Bulge Characterization by Stacking and Flexibility", J. Mol. Biol. (2003) 326, pp. 189-201.
Gerdeman, et al., "In Vitro structure-function studies of the *Bacillus subtilis tyrS* mRNA antiterminator: evidence for factor-independent tRNA acceptor stem binding specificity", Nucleic Acids Research, 2002, vol. 30, No. 4, 1065-1072.
Yanofsky, "Transcription Attenuation: Once Viewed as a Novel Regulatory Strategy", Journal of Bacteriology, Jan. 2000 pp 1-8.

Gollnick et al., "Transcription attenuation", Biochimica et Biophysica Acta 1577 (2002) pp. 240-250.
Henkin, "Transcription termination control in bacteria", Current Opinion in Microbiology 2000, 3: pp. 149-153.
Barbieri et al., Analysis of the *Bacillus subtillis* genome sequence reveals nine new T-box leaders, 1998 Blackwell Science Ltd., Molecular Microbiology, 29, pp. 661-664.
van de Guchte, et al., "Identity elements in tRNA-mediated transcription antitermination: implication of tRNA D-and T-arms in mRNA recognition", Microbiology (2001), 147, pp. 1223-1233.
Kunst, et al., "The complete genome sequence of the Gram-positive bacterium *Bacillus subtilis*", Nature, vol. 390, Nov. 20, 1997, pp. 249-256.
Grundy, et al., "Sequence requirements for terminators and antiterminators in the T box transcription antitermination system: disparity between conservation and functional requirements", Nucleic Acids Research, 2002, vol. 30, No. 7, pp. 1646-1655.
Henkin, "Control of Transcription Termination on Prokaryotes,", Annu. Rev. Genet. 1996, 30: pp. 35-57.
Henkin, et al., "Regulation by transcription attenuation in bacteria: how RNA provides instructions for transcription termination/antitermination decisions", BioEssays 24: pp. 700-707 (2002).
Grundy et al., "The *Staphylococcus aureus ileS*Gene, Encoding Isoleucyl-tRNA Synthetase, Is a Member of the T-Box Family", Journal of Bacteriology, Jun. 1997, pp. 3767-3772.
Putzer, et al., "Transfer RNA-mediated antitermination in vitro "Nucleic Acids Research, 2002, vol. 30, No. 14, pp. 3026-3033.
Wagar, et al., "The Glycyl-tRNA Synthetase of *Chlamydia trachomatis*", Journal of Bacteriology, Sep. 1995, pp. 5179-5185.
Yousef, et al., "trNA requirements for glyQS antitermination: A new twist on tRNA". RNA, vol. 9, No. 9, pp. 1148-1156, (2003).

*Primary Examiner*—Taofiq Solola
(74) *Attorney, Agent, or Firm*—Calfee, Halter & Griswold, LLP

(57) ABSTRACT

Compounds that are selective binding agents specific for RNA secondary and tertiary structures and a fluorescence assay for detecting the binding of small molecules to T-box antiterminator model mRNAs. The compounds include novel tri-substituted oxazolidinones and amino alcohols. The assay provides fluorescently labeled model mRNAs that include conserved sequence information typical of antiterminator bulge regions found in the mRNA of T-box gene regulatory systems.

11 Claims, 2 Drawing Sheets

COMPOSITIONS THAT BIND ANTITERMINATOR RNA AND ASSAY FOR SCREENING SUCH COMPOSITIONS

CROSS REFERENCE TO RELATED APPLICATION

This application claims the benefit of U.S. Provisional Application No. 60/314, 898, filed Aug. 24, 2001, entitled "Inhibition of tRNA-Antiterminator Bulge Complex Formation," the disclosure of which is incorporated as if fully rewritten herein.

FIELD OF THE INVENTION

The present invention relates generally to compounds that bind RNA molecules, and specifically to compounds that bind the antiterminator structure which occurs in the mRNA of T-box gene transcription regulation systems.

BACKGROUND OF THE INVENTION

Ribonucleic acid (RNA) is a biopolymer composed of individual monomers known as nucleotides. These nucleotides are composed of a ribofuranose ring, one of four bases, and a phosphate. The four bases that are most commonly found in RNA are adenosine (A), guanosine (G), cytosine (C), and uridine (U). RNA is most commonly used in the cell as a genetic code messenger RNA (mRNA) or as components in protein synthesis, i.e., ribosomal RNA (rRNA) and transfer RNA (tRNA). Ribonucleic acid has also been found to act as catalytic agents known as "ribozymes" and to interact with various proteins.

RNA has three different levels of structure: primary, secondary, and tertiary. The primary structure represents the specific sequence of the nucleotides found in a given RNA molecule. The secondary structure forms as the result of Watson-Crick pairing between the bases of the primary structure. Various secondary structures are formed from these base pairing interactions; such structures include: hairpin loops, internal loops, bulges, junctions, single strands, and double helices. The tertiary structure forms as the result of interactions between the various secondary structures. Tertiary structures include pseudoknots, triple helices, and loop-helix interactions.

Certain molecular interactions are important in the formation of the secondary and tertiary structures in RNA. Hydrogen bonding is involved in the formation of the Watson-Crick base pairs, which are most prevalent in the helical regions of normal A-form RNA. Stacking interactions between the bases of the RNA contribute to the stability of the RNA in both straight and helical RNA. The formation of non-canonical base pairs is also an important contributor to the formation of the tertiary structure.

Despite its many cellular functions, RNA has not, until recently, been focused upon as a potential target for drug intervention in certain diseases. Because of the numerous cellular functions of RNA, drug intervention at certain steps in cellular processes that involve RNA may prevent protein expression or other RNA-RNA interactions that are important for cellular function and/or bacterial or viral propagation.

Various small molecules have been studied for potential interaction with RNA. For example, the aminoglycosides are known to bind rRNA and to inhibit the group I intron self-splicing reaction and the hammerhead ribozyme cleavage reaction. The oxazolidinones have been shown to bind to the rRNA of the large ribosomal subunit of Gram-positive bacteria. This research is particularly important because Gram-positive bacteria such as *Staphylococcus aureus, Streptococcus pneumoniae,* and *Enterococcus faecium* are becoming serious health threats due to the antibiotic resistance developing in many strains of bacteria. Thus, due to the increasing trend of antibiotic resistance, more research is necessary to develop new, effective drugs for fighting antibiotic resistant microbial strains.

Certain gram-positive bacteria contain a unique mechanism which controls the transcription of certain genes coding for aminoacyl-tRNA synthetase, amino acid biosynthesis, and amino acid transport genes. These so called T-box genes are regulated by a common transcription antitermination system. The leader regions of the mRNA associated with these genes contain many conserved primary sequence and secondary structural elements. Specific secondary structural elements of this leader region form mutually exclusive structures known as the terminator and the antiterminator. The crucial element for controlling gene expression is the transcriptional terminator. Direct interaction between a cognate uncharged tRNA and the leader region of the mRNA triggers formation of an alternate antiterminator structure.

The specificity of the regulatory response is directed primarily by pairing of the anticodon of the tRNA with a single codon displayed at a precise position within the complex leader mRNA structure, i.e., Stem I. (see FIG. 1). A second pairing between the acceptor end of the tRNA and a conserved side-bulge region of the antiterminator structure is also required for readthrough of the mRNA. The interaction of the tRNA acceptor stem with the bulge of the antiterminator is accomplished through base pairing between the nucleotides of the acceptor stem and the nucleotides of the bulge. This second interaction presumably stabilizes the antiterminator, thereby promoting formation of the competing antiterminator structure over formation of the terminator structure. Formation of the terminator structure prevents readthrough of the mRNA (see FIG. 2).

RNA bulge loops are the disruption of an otherwise continuous helix by a single stranded region. Bulges are capable of distorting the helical backbone of RNA which can expose hydrogen bonding surfaces of the bases for interaction with other molecules such as proteins or small molecules. RNA bulges can result in sharp turns in the phosphate backbone, which often results in unfavorable electrostatic interactions as phosphate groups move closer to one another. These unfavorable electrostatic interactions create a unique spatial arrangement of charge to which positively charged molecules can bind.

The T-box system, originally discovered in a single gene in *Bacillus subtilis,* has been found in 19 transcription units in this organism, and has also been uncovered in a variety of Gram-positive bacteria, including *Clostridium, Lactococcus, Lactobacillus, Enterococcus, Staphylococcus, Streptoccus, Deinococcus, Mycobacterium,* and *Corynebacterium.* This list includes a number of important human pathogens. Given that aminoacyl-tRNA synthetase genes are essential for proper charging of the tRNA and cell viability, the T-box system, in particular the antiterminator bulge, provides an intriguing potential target for drug discovery. Thus, there is a need to identify compounds that interact with mRNA secondary structures and potentially disrupt or inhibit the formation of vital tertiary structures in mRNA.

SUMMARY OF THE INVENTION

The present invention provides compounds which are selective binding agents specific for RNA secondary and tertiary structures. The present invention also provides a fluorescence assay for detecting the binding of small molecules to T-box antiterminator model mRNAs. The compounds include novel tri-substituted oxazolidinones and amino alcohols. The assay provides fluorescently labeled model mRNAs that include conserved sequence information typical of antiterminator bulge regions found in the mRNA of T-box gene regulatory systems.

The oxazolidinone compounds of the present invention are not known in the prior art due largely to the challenges of incorporating varied substitutions at C-4 by synthetic means. The amino alcohols of the present invention are not known in the prior art due largely to the lack of methods suitable for incorporating synthetic diversity into synthesized compounds. Furthermore, due to RNA's conformational complexity and structural flexibility, there are few known examples of ligands possessing a high degree of RNA binding selectivity, i.e., exhibiting discrimination between RNA structures having closely related secondary and/or tertiary structures.

Both the tri-substituted oxazolidinones and the amino alcohols of the present invention can selectively bind, modulate, and/or disrupt the function of specific prokaryotic, eukaryotic, viral, fungal and parasitic RNAs by binding to select RNA structural motifs such as bulges, loops, psuedoknots. Thus, the T-box antitermination regulatory RNA elements and ribosomal RNA of bacteria and other organisms are suitable targets for these compounds. Therefore, these compositions may potentially be used as antibacterial, antiviral, anticancer agents, antifungal and antiparasitic agents.

The assay component of the present invention provides a method for individual and high through-put screening of RNA binding ligands that are specific for certain nucleotide sequences in the antiterminator mRNA found in T-box gene regulatory systems, and that may disrupt or inhibit tRNA binding to the antiterminator bulge. An exemplary embodiment of this assay utilizes a fluorescently labeled antiterminator mRNA sequence. The assay is useful for detecting: (i) ligand-antiterminator RNA binding; and (ii) ligand disruption of the functionally relevant binding of tRNA by the antiterminator. Compounds that bind selectively and/or disrupt tRNA binding have the potential to be developed into antibacterial agents. In addition to the oxazolidinones and amino alcohols of the present invention, aminoglycosides, macrotetrolides, nucleic acids and each of their respective analogues may be screened using the assay of the present invention. The assay component of the present invention is not known in the prior art due largely to uncertainty concerning the structural requirements for functional tRNA binding by the antiterminator.

Further advantages of the present invention will become apparent to those of ordinary skill in the art upon reading and understanding the following detailed description of the preferred embodiments.

DETAILED DESCRIPTION OF THE INVENTION

Figure 1:
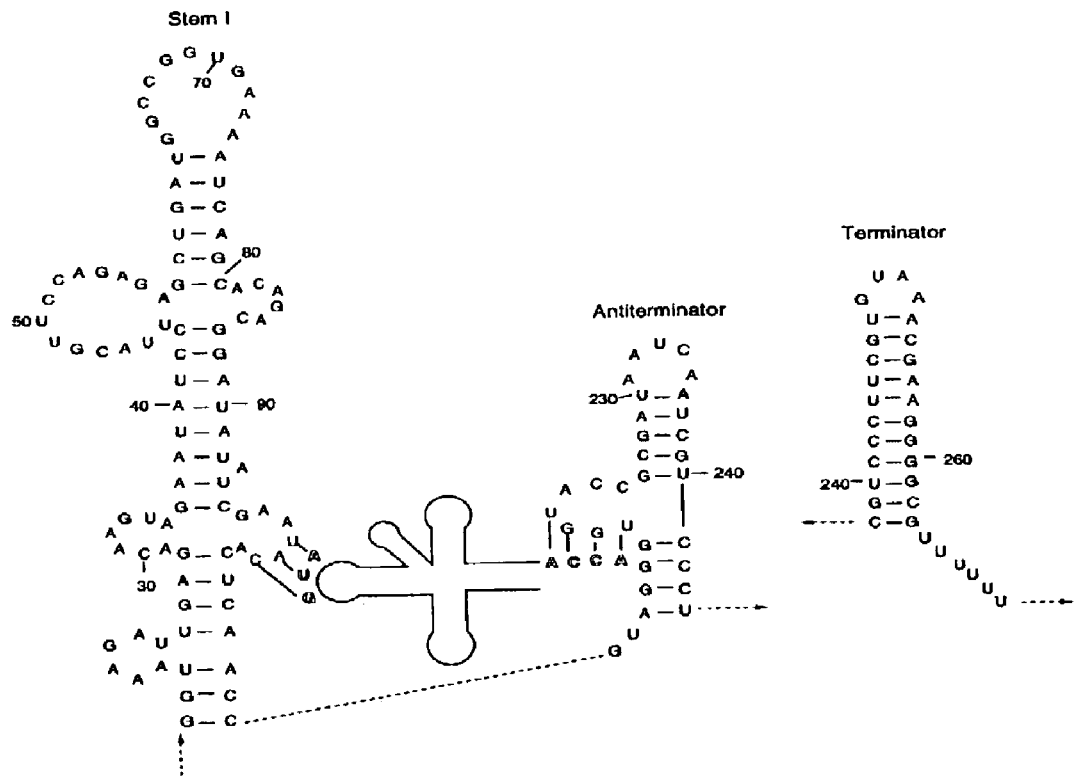
FIG. 1 is a graphic representation of the primary sequence and secondary structure of the mRNA leader region of tyrS showing the Stem I structure, the bulge region of the antiterminator, and a cognate uncharged tRNA bound to both Stem I and the bulge region of the antiterminator. (Grundy and Henkin, *Cell* 74, 475–482, 1993).
Figure 2:
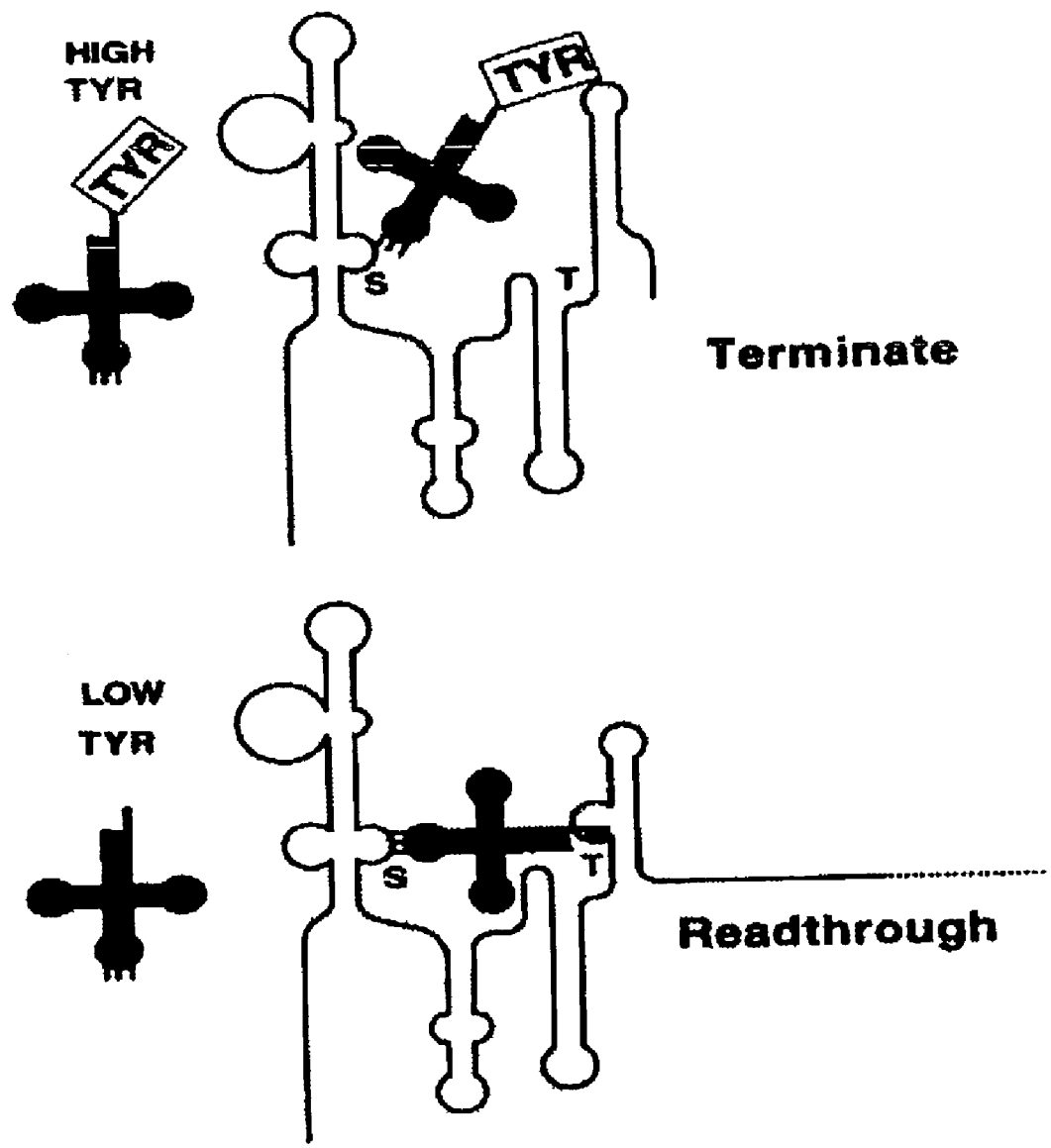
FIG. 2 is a graphic representation of tyrS induction by an uncharged tyrosyl-tRNA showing both the transcription terminate configuration and the readthrough configuration of the T-box regulatory system (Henkin, *Mol. Micrbiol.* 13(3), 381–387, 1994).

An exemplary embodiment of the present invention provides (i) two classes of compounds which are selective binding agents specific for RNA secondary and tertiary structures; and (ii) a fluorescence assay for detecting the binding of small molecules to T-box antiterminator model RNAs. The compounds include novel tri-substituted oxazolidinones and amino alcohols that bind to the bulge region of the antiterminator and disrupt the binding of the cognate tRNA to the bulge (see FIG. 1). The assay provides fluorescently labeled model RNAs that include conserved sequence information typical of antiterminator bulges found in T-Box gene regulatory systems.

I. Compositions that Bind Antiterminator RNA

A. Tri-Substituted Oxazolidinones

The compounds of the present invention are selective ribonucleic acid (RNA) binding agents, specific for RNA secondary and tertiary structure. The first selective RNA binding agents are trisubstituted oxazolidinones of Formula I:

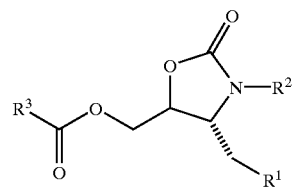

wherein $R^1$ is selected from alkyl, aryl, alkylaryl, and arylalkyl. According to the present invention, when $R^1$ is alkyl, it can be a hydrocarbon or heteroalkyl, and can be linear, branched, cyclic, or multicyclic. When $R^1$ is aryl, it can be a hydrocarbon or heteroaryl; and can be monocyclic or polycyclic, polycyclic aromatics may or may not be fused. $R^1$, whether aromatic or aliphatic, can also be substituted at any substitutable position, with, for example, further alkyl or aryl substituents or halogens. Other substituents would be apparent to those of skill in the art. $R^2$ is selected from the group consisting of alkyl, aryl, alkylaryl, arylalkyl, alkoxy, ester, alcohol, and amide and is chosen such that the carbon that attaches to the oxazoline N is not sterically hindered. $R^3$ is an aliphatic residue and can be substituted at any substitutable position with, for example, alkyl, haloalkyl, cycloalkyl, or aryl substituents, as well as other substituents known to those of skill in the art.

Table 1, below, lists possible substitutions for $R^1$, $R^2$, and $R^3$ as well as the molecular weight for each synthesized compound.

TABLE 1

R Group Substituents for the Tri-Substituted Oxazolidinones.

| No. | R¹ | R² | R³ | MW (M⁺) |
|---|---|---|---|---|
| 1 | Ph | Ph-2-CO$_2$Me | CH$_2$Ph | 459.265 (459) |
| 2 | Ph | Ph-2-CO$_2$Me | c-C$_6$H$_{11}$ | 451.415 (451) |
| 3 | Ph | Ph-2-CO$_2$Me | (CH$_2$)$_6$CH$_3$ | 468.479 (468) |
| 4 | Ph | Ph-4-OMe | CH$_2$Ph | 431.687 (431) |
| 5 | Ph | Ph-4-OMe | c-C$_6$H$_{11}$ | 424.168 (424) |
| 6 | Ph | Ph-4-OMe | (CH$_2$)$_6$CH$_3$ | 440.947 (440) |
| 7 | Ph | nBu | CH$_2$Ph | 381.647 (381) |
| 8 | Ph | nBu | c-C$_6$H$_{11}$ | 372.264 (372) |
| 9 | Ph | nBu | (CH$_2$)$_6$CH$_3$ | 390.486 (390) |
| 10 | CH$_2$CH$_2$Ph | Ph-2-CO$_2$Me | CH$_2$Ph | 448.549 (448) |
| 11 | CH$_2$CH$_2$Ph | Ph-2-CO$_2$Me | c-C$_6$H$_{11}$ | 479.164 (479) |
| 12 | CH$_2$CH$_2$Ph | Ph-2-CO$_2$Me | (CH$_2$)$_6$CH$_3$ | 496.347 (496) |
| 13 | CH$_2$CH$_2$Ph | Ph-4-OMe | CH$_2$Ph | 460.187 (460) |
| 14 | CH$_2$CH$_2$Ph | Ph-4-OMe | c-C$_6$H$_{11}$ | 452.379 (452) |
| 15 | CH$_2$CH$_2$Ph | Ph-4-OMe | (CH$_2$)$_6$CH$_3$ | 462.439 (462) |
| 16 | CH$_2$CH$_2$Ph | nBu | CH$_2$Ph | 410.024 (410) |
| 17 | CH$_2$CH$_2$Ph | nBu | c-C$_6$H$_{11}$ | 402.103 (402) |
| 18 | CH$_2$CH$_2$Ph | nBu | (CH$_2$)$_6$CH$_3$ | 418.761 (418) |
| 19 | c-C$_6$H$_{11}$ | Ph-2-CO$_2$Me | CH$_2$Ph | 466.176 (466) |
| 20 | c-C$_6$H$_{11}$ | Ph-2-CO$_2$Me | c-C$_6$H$_{11}$ | 458.243 (458) |
| 21 | c-C$_6$H$_{11}$ | Ph-2-CO$_2$Me | (CH$_2$)$_6$CH$_3$ | 474.276 (474) |
| 22 | c-C$_6$H$_{11}$ | Ph-4-OMe | CH$_2$Ph | 438.416 (438) |
| 23 | c-C$_6$H$_{11}$ | Ph-4-OMe | c-C$_6$H$_{11}$ | 430.135 (430) |
| 24 | c-C$_6$H$_{11}$ | Ph-4-OMe | (CH$_2$)$_6$CH$_3$ | 446.715 (446) |
| 25 | c-C$_6$H$_{11}$ | nBu | CH$_2$Ph | 388.621 (388) |
| 26 | c-C$_6$H$_{11}$ | nBu | c-C$_6$H$_{11}$ | 380.048 (380) |
| 27 | c-C$_6$H$_{11}$ | nBu | (CH$_2$)$_6$CH$_3$ | 396.164 (396) |

Of the 27 compounds listed in Table 1, compounds 7–9, 16–18, and 25–27 where prepared according to the exemplary method of Example 1, below. Compounds 1–6, 10–15, and 19–24 where prepared according to the exemplary method of Example 2, below.

EXAMPLE 1

CuCN (0.16 mmol) was suspended in Et$_2$O (10 mL) and cooled to −30° C. Phenylmagnesium bromide (3.2 mmol) was added and the reaction stirred at −30° C. for 10 min. (Triphenylmethoxymethyl)-1-oxa-3-azabicyclo[3.1.0]hexan-2-one (0.40 mmol) was added and the reaction was warmed to 0° C. and stirred for 3 hours. The flask was warmed to room temperature and stirred for an additional 3 hours. A pH 9 solution of NH$_4$OH/NH$_4$Cl was added and the reaction extracted with EtOAc (2×), washed with water (2×), brine (2×), dried over MgSO$_4$, filtered, and concentrated to give the desired product as a yellow oil. The crude material was dissolved in THF (8 mL). KF/Al$_2$O$_3$ (738 mg of 40 wt %, 5.08 mmol, ground to a fine powder) and bromobutane (0.04 mL, 0.42 mmol) were added. The reaction was stirred rapidly at room temperature for 24 hours. The reaction was filtered and concentrated to give the desired product as a yellow oil. The oxazolidinone was dissolved in CH$_2$Cl$_2$(3 mL) and cooled to 0° C. Octanoyl chloride (0.8 mmol) was added and the reaction stirred at room temperature for 24 hours. The reaction was washed with saturated NaHCO$_3$, H$_2$O, brine, dried over MgSO$_4$, filtered, and concentrated to give 77 mg of octanoic acid 4-benzyl-3-butyl-2-oxo-oxazolidin-5-ylmethyl ester as a yellow oil. $^1$H NMR: 1.0 (m, 9H), 1.2 (m, 15 H), 1.8 (dd, J=4,7.75 Hz, 2 H), 2.2 (d, J=10.75 Hz, 2 H), 2.6 (d, J=10.75 Hz, 2 H) 7.0 (m, 4H).

EXAMPLE 2

CuCN (0.16 mmol) was suspended in Et$_2$O (3 mL) and cooled to −30° C. Phenylmagnesium bromide (3.2 mmol) was added and the reaction stirred at −30° C. for 10 min. Triphenylmethoxymethyl)-1-oxa-3-azabicyclo[3.1.0]hexan-2-one (0.40 mmol) was added and the reaction was warmed to 0° C. and stirred for 3 hours. The flask was warmed to room temperature and stirred for an additional 3 hours. A pH 9 solution of NH$_4$OH/NH$_4$Cl was added and the reaction extracted with EtOAc (2×), washed with water (2×), brine (2×), dried over MgSO$_4$, filtered, and concentrated to give the desired product as a yellow oil. Pd$_2$(dba)$_3$ (3.2 mg, 0.003 mmol), xantphos[22] (6.36 mg, 0.011 mmol), CsCO$_3$(159 mmol), and oxazolidinone were mixed in dioxane (2 mL), the aryl bromide (0.839 mmol) was added and the reaction was heated to 100° C. for 48 hours. The reaction was concentrated and dissolved in a 25% EtOAc in hexanes solution and applied to a prepacked silica gel micro column and filtered to remove the unreacted material. The column was washed with 100% EtOAc to collect desired product. Upon concentration, the product was obtained as a yellow oil. The oxazolidinone was dissolved in CH$_2$Cl$_2$ (3 mL) and cooled to 0° C. Phenylacetyl chloride (0.8 mmol) was added and the reaction stirred at room temperature for 24 hours. The reaction was washed with saturated NaHCO$_3$, H$_2$O, brine, dried over MgSO$_4$, filtered, and concentrated to give 32 mg of 2-(4-benzyl-2-oxo-5-phenylacetoxymethyl-oxazolidin-3-yl)-benzoic acid methyl ester as a yellow oil. $^1$H NMR: 1.0 (s, 3 H), 1.8 (dd, J=4,7.75 Hz, 2 H), 2.2 (d, J=8.25 Hz, 2 H), 2.2(d, J=10.75 Hz, 2 H), 3.4 (s, 2 H), 6.8 (m, 5 H), 7.0 (m, 5 H), 7.4 (m, 4 H).

B. Amino Alcohols

A second set of selective ribonucleic acid (RNA) binding agents, specific for RNA secondary and tertiary structure are the amino alcohols of Formula II:

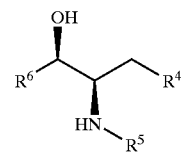

II wherein R$^4$ is selected from alkyl, aryl, alkylaryl, and arylalkyl. According to the present invention, when R$^4$ is alkyl, it can be a hydrocarbon or heteroalkyl, and can be linear, branched, cyclic, or multicyclic. When R$^4$ is aryl, it can be a hydrocarbon or heteroaryl; and can be monocyclic or polycyclic, polycyclic aromatics may or may not be fused. R$^4$, whether aromatic or aliphatic, can also be substituted at any substitutable position, with, for example, further alkyl or aryl substituents or halogens. Other substituents would be apparent to those of skill in the art. R$^5$ is selected from the group consisting of H, alkyl, aryl, alkylaryl, arylalkyl, alkoxy, ester, alcohol, and amide. As with R$^4$, R$^5$ can be substituted at any substitutable position with alkyl, aryl, halo, or other similar substituents. R$^6$ is an aliphatic residue and can be substituted at any substitutable position with, for example, alkyl, haloalkyl, cycloalkyl, or aryl substituents, as well as other substituents known to those of skill in the art.

Table 2, below, lists possible substitutions for R$^4$, R$^5$, and R$^6$ as well as the molecular weight for each synthesized compound.

TABLE 2

R Group Substituents for the Amino Alcohols.

| No. | $R^4$ | $R^5$ | $R^6$ | MW (M⁺) |
|---|---|---|---|---|
| 1 | Ph | nBu | $CH_2OH$ | 237.343 (237) |
| 2 | Ph | H | $CH_2OH$ | 181.235 (181) |
| 3 | $(CH_2)_3CH_3$ | H | $CH_2OH$ | 161.245 (161) |
| 4 | $(CH_2)_5CH_3$ | H | $CH_2OH$ | 189.299 (189) |
| 5 | c-$C_6H_{11}$ | H | $CH_2OH$ | 187.283 (187) |
| 6 | Ph-4-OMe | H | $CH_2OH$ | 211.260 (211) |
| 7 | $CH_2Ph$ | H | $CH_2OH$ | 195.262 (195) |
| 8 | $C(CH_3)CH_2$ | H | $CH_2OH$ | 145.202 (145) |
| 9 | 1-naphthyl | H | $CH_2OH$ | 231.295 (231) |

Of the 9 compounds listed in Table 1, compound 1 was prepared according to the exemplary method of Example 3, below. Compounds 2–9 where prepared according to the exemplary method of Example 4, below.

EXAMPLE 3

4-Benzyl-3-butyl-5-trityloxymethyl-oxazolidin-2-one (0.5 mmol) was dissolved in MeOH:THF (3:1, 0.3 M) and DOWEX 1×8-100 resin (350 mol % of OH form, as purchased the resin was in the chloride form and was washed with 200 mL of 3 M NaOH, 100 mL of $H_2O$, 50 mL of MeOH, and dried overnight under vacuum) was added. The suspension was stirred at room temperature until complete by TLC (18–24 hours), filtered, washed with EtOAc, and concentrated to yield the amino alcohol. The crude product was dissolved in MeOH (5 mL) and DOWEX 50w resin (500 mol %, as purchased the resin was in the sodium form and was washed with 200 mL of 3M HCl, 100 mL of $H_2O$, 50 mL of MeOH and dried overnight under vacuum.) was added. The suspension was stirred at room temperature until complete by TLC (18–24 hours), filtered, washed with MeOH, and concentrated to yield 97 mg of 3-butylamino-4-phenyl-butane-1,2-diol.

EXAMPLE 4

N-(2-aminoethyl)aminomethyl polystyrene (300 mol %, 1% DVB, 1.3 mmol/g from Novabiochem) was washed with THF (25 mL, 3 times) and added to a solution of the 4-Benzyl-5-trityloxymethyl-oxazolidin-2-one (0.5 mmol) in THF (0.3M). The suspension was warmed to 60° C. and stirred until complete (18–24 hours). The reaction was filtered, washed with EtOAc, and concentrated to provide the desired amino alcohol. The crude product was dissolved in MeOH and DOWEX 50w resin (500 mol %, as purchased the resin was in the sodium form and was washed with 200 mL of 3M HCl, 100 mL of $H_2O$, 50 mL of MeOH and dried overnight under vacuum.) was added. The suspension was stirred at room temperature until complete by TLC (18–24 hours), filtered, washed with MeOH, and concentrated to yield 82 mg of 3-amino-4-phenyl-butane-1,2-diol.

The starting materials in Examples 1–4 were prepared according to the following exemplary method:

A substituted allylic alcohol (e.g. 1-(Triphenylmethoxy)-3-buten-2-ol, 9.5 mmol) was dissolved in benzene (4.5 mL). Pyridine (2.3 mL, 28.5 mmol) and p-nitrophenylchloroformate (3.83 g, 19.0 mmol) were added and the reaction was stirred at room temperature for 4 hours. The reaction was diluted with EtOAc and washed with saturated $NaHCO_3$ (2×), brine (2×), dried over $MgSO_4$, filtered, and concentrated. Thourse crude product was then dissolved in DMF (64 mL) and $NaN_3$ (6.18 g, 95.0 mmol) was added. The reaction was heated to 35° C. and stirred for 18 hours. The reaction was diluted with EtOAc and washed with $NH_4Cl$ (2×), brine (2×), dried over $MgSO_4$, filtered, and concentrated. The product was chromatographed (2% EtOAc in hexanes) giving 2.98 g of the product (79%), as a yellow oil. The azidoformate (1.93 g, 4.83 mmol) was dissolved in $CH_2Cl_2$(40 mL). The solution was transferred to a sealed tube which was cooled to −78° C., evacuated of air, and sealed. The tube was heated to 109° C. for 13 hours. The tube was cooled and opened. The resulting precipitate was then filtered to give 1.2 g of (triphenylmethoxymethyl)-1-oxa-3-azabicyclo[3.1.0]hexan-2-one (50%) as a white powder, mp 205–206° C.

C. General Method for Synthesizing Compounds

The present invention further relates to methods of making the trisubstituted oxazolidinones and amino alcohols, the method comprising the steps of: (a) providing a substituted allylic alcohol of Formula A:

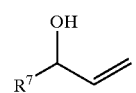

wherein $R^7$ is selected from the group consisting of alkyl and aryl, and ester; (b) converting compound 1 to an azidoformate; (c) heating the resulting azidoformate for a sufficient time at a sufficient temperature to provide an aziridine; (d) adding $R^1$ to the aziridine through a suitable reaction; (e) adding $R^2$-X to the resulting compound, wherein X is a halide, to provide substitution $R^2$ on the oxazoline N atom; and (f) optionally, adding an $R^3$-acid chloride to produce the trisubstituted oxazolidinone compound of Formula I. Preferably, $R^1$ is added to the aziridine through a Grignard reaction. The present invention further comprises a method of converting the trisubstituted oxazolidinone to a trisubstituted amino alcohol comprising the step of hydrolyzing the trisubstituted oxazolidinone to provide a trisubstituted amino alcohol.

Thus, the trisubstituted oxazolidinones of the present invention can be prepared by the following reaction scheme:

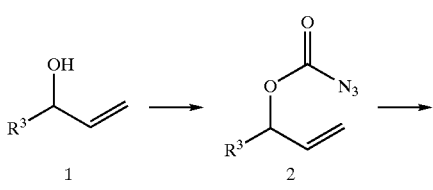

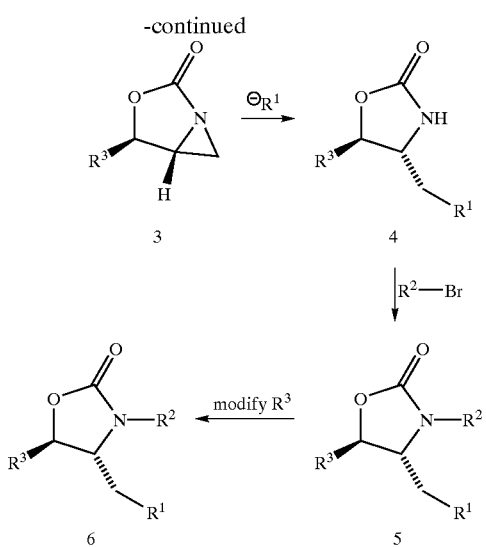

According to this scheme;, start with compound 1 and convert it to azidoformate 2. Heating compound 2 provides aziridine 3. Start with $R^3$ on compound 1; this $R^3$ can either be the $R^3$ in the final compound (e.g. 6) or $R^3$ can be modified by adding acid chloride. Add $R^1$ (typically as a Grignard reagent) to compound 3 to produce 4. $R^1$ can be any nucleophilic reagent (alcohols, amines, thiols, carboxylic acids). The substitution on $R^1$ should be stable to the formation/reaction of a Grignard reagent. Add $R^2$ in the form of an alkyl or aryl halide to form 5. The only restriction concerning the substitution on $R^2$ is that it cannot contain an unsubstituted amide (as in compound 4). Finally modify $R^3$ of 5 by adding an acid chloride to produce a compound 6 with a different $R^3$ than was present initially. The resulting trisubstituted oxazolidinone can be converted to a trisubstituted amino alcohol through a subsequent hydrolysis reaction. All examples disclosed herein are for illustrative purposes only and are not to be construed in a limiting sense.

D. Alternate Substituents

Compounds prepared in accordance with the present invention are not particularly limited with respect to substituents that can be present on the R groups, $R^1$, $R^2$, $R^3$, $R^4$, $R^5$, and $R^6$. $R^1$–$R^6$ can be substituted at any substitutable position with such substituents as alkyl, aryl, halo, and so forth. The substituents on $R^1$–$R^6$ can be virtually any substituent group, and suitable substituents would be recognized by those of ordinary skill in the art.

The term "aliphatic" refers to acyclic or cyclic, saturated or unsaturated carbon compounds, excluding aromatic compounds. "Aliphatic" groups include linear, branched, cyclic, and polycyclic alkyl, alkenyl, and alkynyl radicals.

Where the term alkyl is used, either alone or with other terms, such as haloalkyl or alkylaryl, it includes $C_1$ to $C_{12}$ linear or branched alkyl radicals, examples include methyl, ethyl, propyl, isopropyl, butyl, tert-butyl, and so forth. Also included in the term "alkyl" are cyclic, multicyclic, and heterocyclic alkyl groups. The term "haloalkyl" includes $C_1$ to $C_{10}$ linear or branched alkyl radicals substituted with one or more halo radicals. Some examples of haloalkyl radicals include trifluoromethyl, 1,2-dichloroethyl,3-bromopropyl, and so forth. The term "halo" includes radicals selected from F, Cl, Br, and I. Alkyl radical substituents of the present invention may also be substituted with other groups; suitable substituents would be recognized by those of ordinary skill in the art.

The term aryl, used alone or in combination with other terms such as alkylaryl, haloaryl, or haloalkylaryl, includes such aromatic radicals as phenyl, biphenyl, and benzyl, as well as fused aryl radicals such as naphthyl, anthryl, phenanthrenyl, fluorenyl, and indenyl on so forth. The term "aryl" also encompasses "heteroaryls," which are aryls that have carbon and one or more heteroatoms, such as O, N, or S in the aromatic ring. Examples of heteroaryls include indolyl, pyrrolyl, and so on. "Alkylaryl" or "arylalkyl" refers to alkyl-substituted aryl groups such as butylphenyl, propylphenyl, ethylphenyl, methylphenyl, 3,5-dimethylphenyl, tert-butylphenyl and so forth. As used herein, the term "alkylaryl" connotes an alkyl group with one or more aromatic substituents, and "arylalkyl" connotes an aryl group with one or more alkyl substituents. "Haloaryl" refers to aryl radicals in which one or more substitutable positions has been substituted with a halo radical, examples include fluorophenyl, 4-chlorophenyl, 2,5-chlorophenyl and so forth. "Haloalkylaryl" refers to aryl radicals that have a haloalkyl substituent. Examples of haloalkylaryls include such radicals as bromomethylphenyl, 4-bromobutylphenyl and so on.

Also included in the family of compounds of Formulae I and II are the pharmaceutically acceptable salts thereof. The phrase "pharmaceutically acceptable salts" connotes salts commonly used to form alkali metal salts and to form addition salts of free acids or free bases. The nature of the salt is not critical, provided that it is pharmaceutically acceptable. Suitable pharmaceutically acceptable acid addition salts of compounds of Formulae I and II may be prepared from an inorganic acid or from an organic acid. Examples of such inorganic acids are hydrochloric, hydrobromic, hydroiodic, nitric, carbonic, sulfuric, and phosphoric acid. Appropriate organic acids may be selected from aliphatic, cycloaliphatic, aromatic, araliphatic, heterocyclic, carboxylic, and sulfonic classes of organic acids, examples of which include formic, acetic, propionic, succinic, glycolic, gluconic, lactic, malic, tartaric, citric, ascorbic, glucoronic, maleic, fumaric, pyruvic, aspartic, glutamic, benzoic, anthranilic, mesylic, salicylic, p-hydroxybenzoic, phenylacetic, mandelic, ambonic, pamoic, methanesulfonic, ethanesulfonic, benzenesulfonic, pantothenic, 2-hydroxyethanesulfonic, toluenesulfonic, sulfanilic, cyclohexylaminosulfonic, stearic, algenic, β-hydroxybutyric, galactaric, and galacturonic acids. Suitable pharmaceutically acceptable base addition salts of compounds of Formulae I and II include metallic salts made from aluminum, calcium, lithium, magnesium, potassium, sodium, and zinc. Alternatively, organic salts made from N,N'-dibenzylethylenediamine, chloroprocaine, choline, diethanolamine, ethylenediamine, meglumine (N-methylglucamine) and procaine may be used form base addition salts of the compounds of Formulae I and II. All of these salts may be prepared by conventional means from the corresponding compounds of Formulae I and II by reacting, for example, the appropriate acid or base with the compound of Formula I or II.

Derivatives are intended to encompass any compounds which are structurally related to the compounds of Formulae I and II or which possess the substantially equivalent activity, as measured by the derivative's ability to selectively bind to RNA secondary and tertiary structures. By way of example, such compounds may include, but are not limited to, prodrugs thereof. Such compounds can be formed in vivo, such as by metabolic mechanisms.

E. Use of Synthesized Compounds

The terms "therapeutically effective" and "pharmacologically effective" are intended to qualify the amount of each agent which will achieve the goal of improvement in disease severity and the frequency of incidence over treatment of each agent by itself, while avoiding adverse side effects typically associated with alternative therapies.

The term "subject" for purposes of treatment includes any human or animal subject in need of antibacterial, antiviral, anticancer, antifungal, or antiparasitic treatment. For methods of prevention the subject is any human or animal subject, and preferably is a human subject who is at risk coming into contact with undesirable microorganisms, such as bacterium, virus, fungus, or parasite. Besides being useful for human treatment, the compounds of the present invention are also useful for veterinary treatment of mammals, including companion animals and farm animals, such as, but not limited to dogs, cats, horses, cows, sheep, and pigs. Preferably, subject means a human.

As used herein, the term "treatment" includes partial or total disruption of RNA function of undesirable microorganisms, such as undesirable prokaryotic and eukaryotic cells, viruses, fungi, and parasites, with minimal disruptive effects on normal cells. The term "prevention" includes either preventing the onset of a clinically evident condition caused by unwanted microorganisms altogether or preventing the onset of a preclinically evident stage of a condition caused by microorganisms in individuals at risk. This includes prophylactic treatment for those at risk of coming into contact with undesirable microorganisms. When used for preventative treatment, the pharmaceutical compositions of the present invention may be administered to the subject either prior to or after exposure to the undesirable microorganism.

In one aspect, the present invention comprises a pharmaceutical composition with an active ingredient of Formula I or II that can selectively bind an disrupt the function of the RNA of specific microorganisms, including prokaryotic, eukaryotic, viral, fungal, and parasitic RNA. Pharmaceutical compositions made with compounds of the present invention are useful as antibacterial, antiviral, anticancer, antifungal, and antiparasitic agents.

The administration of the present invention may be for either prevention or treatment purposes. The methods and compositions used herein may be used alone or in conjunction with additional therapies known to those skilled in the art. Alternatively, the methods and compositions described herein may be used as adjunct therapy. By way of example, when used as an anticancer agent, the compounds of the present invention may be administered alone or in conjunction with other antineoplastic agents or other growth inhibiting agents or other drugs or nutrients.

The phrase "adjunct therapy" (or "combination therapy"), in defining use of a compound of the present invention and one or more other pharmaceutical agent, is intended to embrace administration of each agent in a sequential manner in a regimen that will provide beneficial effects of the drug combination, and is intended as well to embrace co-administration of these agents in a substantially simultaneous manner, such as in a single formulation having a fixed ratio of these active agents, or in multiple, separate formulations for each agent.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are capsules, tablets, powders, granules or a suspension, with conventional additives such as lactose, mannitol, corn starch or potato starch; with binders such as crystalline cellulose, cellulose derivatives, acacia, corn starch or gelatins; with disintegrators such as corn starch, potato starch or sodium carboxymethyl-cellulose; and with lubricants such as talc or magnesium stearate. The active ingredient may also be administered by injection as a composition wherein, for example, saline, dextrose or water may be used as a suitable carrier.

For intravenous, intramuscular, subcutaneous, or intraperitoneal administration, the compound may be combined with a sterile aqueous solution which is preferably isotonic with the blood of the recipient. Such formulations may be prepared by dissolving solid active ingredient in water containing physiologically compatible substances such as sodium chloride, glycine, and the like, and having a buffered pH compatible with physiological conditions to produce an aqueous solution, and rendering said solution sterile. The formulations may be present in unit or multi-dose containers such as sealed ampoules or vials.

When treating microorganisms localized in the gastrointestinal tract, the compound may be formulated with acid-stable, base-labile coatings known in the art which begin to dissolve in the high pH small intestine. Formulation to enhance local pharmacologic effects and reduce systemic uptake are preferred.

Formulations suitable for parenteral administration conveniently comprise a sterile aqueous preparation of the active compound which is preferably made isotonic. Preparations for injections may also be formulated by suspending or emulsifying the compounds in non-aqueous solvent, such as vegetable oil, synthetic aliphatic acid glycerides, esters of higher aliphatic acids or propylene glycol.

Formulations for topical use include known gels, creams, oils, and the like. For aerosol delivery, the compounds may be formulated with known aerosol excipients, such as saline, and administered using commercially available nebulizers. Formulation in a fatty acid source may be used to enhance biocompatibility.

For rectal administration, the active ingredient may be formulated into suppositories using bases which are solid at room temperature and melt or dissolve at body temperature. Commonly used bases include coca butter, glycerinated gelatin, hydrogenated vegetable oil, polyethylene glycols of various molecular weights, and fatty esters of polyethylene stearate.

The dosage form and amount can be readily established by reference to known treatment or prophylactic regiments. The amount of therapeutically active compound that is administered and the dosage regimen for treating a disease condition with the compounds and/or compositions of this invention depends on a variety of factors, including the age, weight, sex, and medical condition of the subject, the severity of the disease, the route and frequency of administration, and the particular compound employed, the location of the unwanted microorganisms, as well as the pharmacokinetic properties of the individual treated, and thus may vary widely. The dosage will generally be lower if the compounds are administered locally rather than systemically, and for prevention rather than for treatment. Such treatments may be administered as often as necessary and for the period of time judged necessary by the treating physician. One of skill in the art will appreciate that the dosage regime or therapeutically effective amount of the inhibitor to be administrated may need to be optimized for each individual. The pharmaceutical compositions may contain active ingredient in the range of about 0.1 to 2000 mg, preferably in the range of about 0.5 to 500 mg and most preferably between about 1 and 200 mg. A daily dose of about 0.01 to 100 mg/kg body weight, preferably between about 0.1 and about 50 mg/kg body weight, may be appropriate. The daily dose can be administered in one to four doses per day.

In another aspect, the compounds of the present invention may be formulated with a suitable carrier to form a disinfecting composition useful for the purpose of disinfecting surfaces that have or may come into contact with undesired microorganisms. The disinfecting composition comprises an effective amount of a compound of Formula I or II, or a combination thereof, to selectively disrupt the function of specific, undesirable prokaryotic, eukaryotic, viral, fungal, and parasitic RNA. Suitable carriers can be chosen to formulate the compounds of Formulae I and II into antiviral and/or antibacterial soaps, gels, lotions, creams, sprays, and the like for use on a subject's skin. In another aspect of the present invention, the compounds of Formulae I and II, and combinations thereof, can be formulated with suitable carriers to use in disinfectant cleaners and disinfectant agents for household, hospital, and/or industrial use.

The present invention further comprises methods of using the compounds of the present invention to selectively bind and disrupt the function of specific prokaryotic, eukaryotic, viral, fungal, and parasitic RNA. Specifically, the present invention comprises a method of inhibiting replication of microorganisms in a subject, comprising introducing a therapeutically effective amount of a compound of Formula I or II to a subject in need of such treatment, wherein the microorganism is selected from the group consisting of bacteria, viruses, fungus, and parasites. The invention further comprises a method of inhibiting the replication of bacteria comprising introducing an effective amount of a compound of Formula I or II to the bacteria whereby the compound selectively binds the T-box antitermination regulatory RNA elements and ribosomal RNA of the bacteria, thereby inhibiting replication of the bacteria. The invention further comprises a method of inhibiting the replication of human immunodeficiency virus (HIV) in a subject in need of such treatment, comprising introducing a therapeutically effective amount of a compound of Formula I or Formula II, or combinations or derivatives thereof to the subject, whereby the compound of Formula I or II selectively binds and disrupts the function of the Rev response element (RRE) and TAR of the HIV, thereby inhibiting replication of the virus. The invention further comprises a method of inhibiting the replication of the human T-cell leukemia virus (HTLV) comprising introducing a therapeutically effective amount of a compound of formula I or II to the virus, whereby the compound selectively binds with the RNA elements of the HTLV thereby inhibiting replication of the virus.

The present invention further comprises a method of disinfecting a surface contaminated with bacteria, viruses, fungus, and parasites, comprising introducing an effective amount of a compound of Formula I or II or a combination thereof to the surface in need of disinfection. In accordance with the present invention, the compounds of Formulae I and II may be incorporated into a carrier vehicle such as a detergent, a cleaning agent, a lotion, a cream, a spray, or other suitable carrier. The disinfecting agent can be used on any surface in need of disinfection, including hands, and surfaces, such as in a kitchen, bathroom, or hospital.

II. Fluorescence Assay for Detecting the Binding of Small Molecules to T-Box Antiterminator Model RNAs The fluorescent assay of the present invention measures the binding of small molecules such as oxazolidinones, amino alcohols, and aminoglycosides to model RNAs. The assay also measures the binding of macromolecules such as nucleic acids such as tRNA and analogs of tRNA such as microhelix or acceptor end tetramer analogs, and other complimentary oligonucleotides to such model RNAs. Both the multi-well assay plate format (e.g., 96 well) and the single cell assay format are compatible with this assay. The experimental conditions described below apply to the single cell assay format.

An exemplary embodiment of the assay of the present invention utilizes fluorescently labeled RNA sequences that are representative of the region of the antiterminator secondary structure that forms the bulge to which the acceptor end of the tRNA binds in a typical T-Box gene regulatory system. These fluorescently labeled model RNAs serve as fluorescent reporters for monitoring ligand, i.e., small molecule and biopolymer binding. A discussion of the design, proof of functional relevance, and structural characteristics of T-box antiterminator model RNAs can be found in Gerdeman, Henkin and Hines, *Nucleic Acids Research;* 1065–1072, 2002, the entire text of which is incorporated by reference herein.

Concerning the exemplary embodiment of the assay component of the present invention, the reporter molecules utilized in the assay included the following model RNA sequences:

```
(RNA I)
5'-GAGGGUGGUACCGCGCUUCGGCGUCCCUC-3'      SEQ ID NO:1

(RNA II)
5'-GAGGGUGGAACCGCGCUUCGGCGUCCCUC-3'      SEQ ID NO:2

(RNA III)
5'-GAGGGUGGUAUCGCGCUUCGGCGUCCCUC-3'      SEQ ID NO:3

(RNA IV)
5'-GAGGGUGGAAUCGCGCUUCGGCGUCCCUC-3'      SEQ ID NO:4
```

It should be noted that the assay of the present invention is not limited to these four model RNAs and may utilize any available model RNA that includes the relevant conserved sequence information, forms the relevant secondary structure in vitro, and that can be fluorescently or otherwise labeled.

The fluorescent labels utilized in the exemplary embodiment include (i) fluorescein-12-ddU added at the 3' end; (ii) a 2'-amino-butyrl-pyrene-U substitution at position 18; and (iii) a 2-aminopurine substitution at position 9 (for RNA II and IV) or position 10 for RNA I through IV. The 3' fluorescein label was attached using a commercially available 3'-end-labeling kit and fluorescein-12-ddUTP. All other fluorescent labeled RNAs are obtainable from commercial custom synthesis sources.

A. General Method

An exemplary embodiment of the assay of the present invention involves the following steps. It is important to note that this is a general method and that this assay is compatible with certain changes in buffer conditions, alternative additives (e.g. polyethylene glycol, DMSO, etc.) and changes in temperature.

(1) A 1.0 ml solution of 600 nM 9-(2-aminopurine)-RNA II or 9-(2-aminopurine)-RNA IV in 0.5×TBE, 50 mM NaCl is renatured by heating to 90° C. for 1.5 minutes followed by cooling to room temperature. (0.5×TBE is 25 mM Tris-borate, pH 8.3, 0.5 mM EDTA).

(2) After cooling, 83.3 μL of labeled RNA solution from step 1 is added to 414.2 μl of 0.5×TBE, 50 mM NaCl, 6 mM MgCl$_2$ to bring the final concentration of labeled RNA to 100 nM in 0.5×TBE, 50 mM NaCl, 5 mM MgCl$_2$.

(3) 200 mM stock solutions of ligand are prepared in N,N-dimethylformamide (DMF) for the oxazolidinones and amino alcohols; and water for the aminoglycosides. When using other biomolecules as the ligand (e.g. a microhelix tRNA mimic) the stocks are prepared in buffer (0.5×TBE, 50 mM NaCl, 5 mM MgCl$_2$).

(4) For the RNA control fluorescence measurements, 2.5 μL of buffer (0.5×TBE, 50 mM NaCl, 5 mM MgCl$_2$) is added to labeled RNA solution from Step 2 for a final volume of 500 ul. After mixing gently, the measurements are performed in a square 500 μL cuvette on a SPEX Fluoromax-2-spectrofluorometer at 20° C. with excitation at 310 nm and collection of emission spectra from 330–450 nm. The fluorescence of buffer alone is also measured.

$F_o$ (fluorescence of labeled RNA alone)=$F_{370\ (labeled\ RNA)}$−$F_{370(buffer)}$.

(5) After adding 2.5 μL of 200 mM stock ligand solution (prepared in Step 3) to an RNA sample from step 2 and gently stirring (leading to a final ligand concentration of 1 mM ligand) the fluorescence is monitored as in step 4. The fluorescence of an identical concentration of ligand in buffer is also measured.

$F$ (fluorescence of labeled RNA with ligand)=$F_{370\ (ligand+labeled\ RNA)}$−$F_{370\ (ligand\ in\ buffer)}$ For dissociation constant ($K_d$) measurements, the same procedure is followed, but with successive 0.1–0.2 μl additions of stock ligand solutions.

B. Results

The results in Tables 3 and 4 were obtained by monitoring the fluorescence of 500 μl of a 100 nM-1 μM solution of 9-(2-aminopurine)-RNA II or a 100 nM solution of 9-(2-aminopurine)-RNA IV by excitation at 310 nm and observing emission spectra from 330–450 nm. Ligand binding was monitored by measuring the change in fluorescence at 370 nm upon addition of ligand. A final ligand concentration of 1 mM was used for initial screens or a range of final concentrations (e.g. 0–300 uM) was used for $K_d$ determinations. Controls included fluorescently labeled RNA in buffer; unlabeled RNA with ligand in buffer; and ligand in buffer. Relative fluorescence ratios (a measure of RNA binding selectivity) were determined by dividing the relative fluorescence of 9-(2-aminopurine)-RNA II in the presence of ligand by relative fluorescence of 9-(2-aminopurine)-RNA IV in the presence of ligand. Relative fluorescence equals F-F$_o$, for each labeled RNA/ligand pair where F and F$_0$ are as defined above in the general method. Thus, for the set of experiments yielding the data in Tables 3 and 4, the relative fluorescence ratio equals (F-F$_o$)$_{9\text{-}(2\text{-}aminopurine)\text{-}RNA\ II}$/(F-F$_o$)$_{9\text{-}(2\text{-}aminopurine)\text{-}RNA\ IV}$.

Example relative fluorescence ratios are 0.4 for amino alcohol #2, indicating that it preferentially binds RNA IV, and 3.6 for oxazolidinone #4 indicating that it preferentially binds RNA II. Thus, a relative fluorescence ratio of less than 1.0 indicates preferential binding for RNA IV, and a relative fluorescence ratio of greater than 1.0 indicates preferential binding for RNA II.

The $K_d$ s for oxazolidinone #4 were determined to be 22 μM for RNA II and 250 μM for RNA IV. These values confirm the selectivity indicated by the relative fluorescence ratio data and indicate a significant degree of selectivity between RNAs II and IV (i.e., RNAs with similar secondary, but different tertiary structures).

TABLE 3

Relative Fluorescence Ratios for the Tri-Substituted Oxazolidinones of Table 1.

| Oxazolidinone # | Relative Fluorescence Ratio |
| --- | --- |
| 1 | 0.678 |
| 2 | 0.533 |
| 3 | 1.117 |
| 4 | 3.580 |
| 5 | 0.956 |
| 6 | 0.638 |
| 7 | 1.321 |
| 8 | 0.822 |
| 9 | 0.846 |
| 10 | 0.711 |
| 11 | 0.909 |
| 12 | 1.583 |
| 13 | 0.758 |
| 14 | 0.921 |
| 15 | 0.906 |
| 16 | 1.033 |
| 17 | 0.839 |
| 18 | 0.821 |
| 19 | 0.501 |
| 20 | 0.762 |
| 21 | 0.479 |
| 22 | 0.681 |
| 23 | 0.746 |
| 24 | 0.750 |
| 25 | 0.741 |
| 26 | 0.782 |
| 27 | 0.692 |

TABLE 4

Relative Fluorescence Ratios for the Amino Alcohols of Table 2.

| Amino Alcohol # | Relative Fluorescence Ratio |
| --- | --- |
| 2 | 0.418 |
| 5 | 0.630 |
| 6 | 0.367 |
| 8 | 0.622 |

The selectivity of the oxazolidinones for RNAs with different tertiary structures was significantly affected by the C-4 substituent (R1) as well as R3. Changes at the C-4 position (e.g. oxazolidinone #4 vs. oxazolidinone #14 vs. oxazolidinone #22 and #3 vs. oxazolidinone #12 vs. oxazolidinone #21) led to drastic changes in the binding selectivity (e.g. relative fluorescence ratio for oxazolidinone #4 equals 3.6, oxazolidinone #14 equals 0.92, and oxazolidinone #22 equals 0.68) indicating that the compounds disclosed here are capable of selective binding of RNA structural motifs.

The assay of the present invention can also be readily modified for use in fluorescence resonance energy transfer (FRET) measurements where the ligand (e.g. a tRNA mimic) is also fluorescently labeled such that the ligand-antiterminator pair is an appropriate fluorescence donor-acceptor pair (e.g. fluorescein on the antiterminator model and tetramethylrhodamine on the ligand). This type of approach would be very useful and sensitive for monitoring disruption of tRNA-antiterminator binding by small molecule ligands. Disruption of the FRET would indicate a ligand that disrupted tRNA-antiterminator binding. This modification of the assay of the present invention would presumably result in a significant increase in sensitivity.

While the above description contains many specificities, these should not be construed as limitations on the scope of the invention, but rather as exemplification of preferred embodiments. Numerous other variations of the present invention are possible, and it is not intended herein to mention all of the possible equivalent forms or ramifications of this invention.

What is claimed:

1. A compound of formula I:

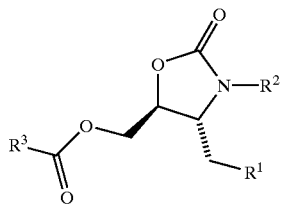

wherein
- R$^1$ is selected from the group consisting of alkyl, aryl, alkylaryl, and arylalkyl;
- R$^2$ is selected from the group consisting of alkyl, aryl, alkylaryl, arylalkyl, alkoxy, ester, alcohol, and amide; and
- R$^3$ is aliphatic or substituted aliphatic, wherein the substituent is selected from the group consisting of alkyl, aryl, and halo.

2. The compound of claim 1, wherein
- R$^1$ is selected from the group consisting of aryl, alkylaryl, arylalkyl, and cycloalkyl;
- R$^2$ is selected from the group consisting of alkyl, aryl, alkylbenzoate, and alkoxyphenyl; and
- R$^3$ is selected from the group consisting of alkyl, cycloalkyl, and alkylaryl.

3. The compound of claim 2, wherein
- R$^1$ is selected from the group consisting of phenyl, 2-(phenyl)ethyl, and cyclohexyl;
- R$^2$ is selected from the group consisting of methyl benzoate, ethyl benzoate, propyl benzoate, butyl benzoate, methoxyphenyl, ethoxyphenyl, propoxyphenyl, butoxyphenyl, C$_1$ to C$_{12}$ alkyl, and aryl;
- R$^3$ is selected from the group consisting of C$_1$ to C$_{12}$ alkyl, cycloalkyl, and alkylphenyl.

4. A method of inhibiting replication of microorganisms in a subject, comprising administering a therapeutically effective amount of a compound of Formula I, or a pharmaceutically acceptable salt thereof, to the subject in need of such treatment, wherein the microorganism is selected from the group consisting of bacteria, viruses, fungi, and parasites.

5. The method of claim 4 wherein the microorganism is bacteria, the method comprising administering an effective amount of a compound of Formula I, or a pharmaceutically acceptable salt thereof, to the subject, whereby the compound selectively binds the T-Box antitermination regulatory RNA elements and ribosomal RNA of the bacteria, thereby inhibiting replication of the bacteria.

6. The method of claim 4 wherein the microorganism is an HIV virus, the method comprising administering a therapeutically effective amount of a compound of Formula I, or a pharmaceutically acceptable salt thereof to the subject, whereby the compound of Formula I selectively binds and disrupts the function of the Rev response element (RRE) and TAR of the HIV, thereby inhibiting replication of the virus.

7. The method of claim 4 wherein the microorganism is a T-cell leukemia virus (HTLV), the method comprising administering a therapeutically effective amount of a compound of Formula I, or a pharmaceutically acceptable salt thereof, to the subject, whereby the compound selectively binds with the RNA elements of the HTLV thereby inhibiting replication of the virus.

8. A method of disinfecting a surface comprising applying an effective amount of a compound of Formula I or combinations thereof to the surface in need of disinfection.

9. A method of preparing a trisubstituted oxazolidinone compound of Formula I:

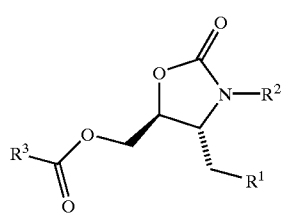

wherein
- R$^1$ is selected from the group consisting of alkyl, aryl, alkylaryl, and arylalkyl;
- R$^2$ is selected from the group consisting of alkyl, aryl, alkylaryl, arylalkyl, alkoxy, ester, alcohol, and amide; and
- R$^3$ is aliphatic or substituted aliphatic, wherein the substituent is selected from the group consisting of alkyl, aryl, and halo;

comprising the steps of:
(a) providing a substituted allylic alcohol of Formula A:

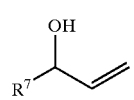

wherein R$^7$ is selected from the group consisting of alkyl, aryl, and ester;

(b) converting the substituted allylic alcohol of Formula A to an azidoformate;

(c) heating the resulting azidoformate for a sufficient time at a sufficient temperature to provide an aziridine;

(d) adding R$^1$ to the aziridine;

(e) adding R$^2$—X to the resulting compound, wherein X is a halide, to provide substitution R$^2$ on the oxazoline N atom; and (f) optionally, adding an R$^3$-acid chloride to produce the trisubstituted oxazolidinone compound of Formula I.

10. The method of claim 9 wherein R$^1$ is added to the aziridine through a Grignard reaction.

11. The method of claim 9 further comprising the step of hydrolyzing the trisubstituted oxazolidinone to provide a trisubstituted amino alcohol.

* * * * *

UNITED STATES PATENT AND TRADEMARK OFFICE
CERTIFICATE OF CORRECTION

| | |
|---|---|
| PATENT NO. | : 7,005,441 B2 |
| APPLICATION NO. | : 10/226614 |
| DATED | : February 28, 2006 |
| INVENTOR(S) | : Jennifer V. Hines et al. |

It is certified that error appears in the above-identified patent and that said Letters Patent is hereby corrected as shown below:

On the Title Page, Item [73] Assignee should read as follows:

Ohio University, Athens, OH (US)
The Ohio State University Research Foundation, Columbus, OH (US)

Signed and Sealed this

Thirteenth Day of November, 2007

JON W. DUDAS
*Director of the United States Patent and Trademark Office*

SEQUENCE LISTING

<160> NUMBER OF SEQ ID NOS: 4

<210> SEQ ID NO 1
<211> LENGTH: 29
<212> TYPE: RNA
<213> ORGANISM: Artificial
<220> FEATURE:
<223> OTHER INFORMATION: synthetic

<400> SEQUENCE: 1
gaggguggua ccgcgcuucg gcgucccuc                                      29

<210> SEQ ID NO 2
<211> LENGTH: 29
<212> TYPE: RNA
<213> ORGANISM: Artificial
<220> FEATURE:
<223> OTHER INFORMATION: synthetic

<400> SEQUENCE: 2
gaggguggaa ccgcgcuucg gcgucccuc                                      29

<210> SEQ ID NO 3
<211> LENGTH: 29
<212> TYPE: RNA
<213> ORGANISM: Artificial
<220> FEATURE:
<223> OTHER INFORMATION: synthetic

<400> SEQUENCE: 3
gaggguggua ucgcgcuucg gcgucccuc                                      29

<210> SEQ ID NO 4
<211> LENGTH: 29
<212> TYPE: RNA
<213> ORGANISM: Artificial
<220> FEATURE:
<223> OTHER INFORMATION: synthetic

<400> SEQUENCE: 4
gaggguggaa ucgcgcuucg gcgucccuc                                      29